United States Patent
Zhang et al.

(10) Patent No.: US 12,305,243 B2
(45) Date of Patent: May 20, 2025

(54) METHOD FOR IDENTIFYING AND EVALUATING TOXIGENIC CAPABILITY OF AFLATOXIGENIC STRAIN

(71) Applicant: OIL CROPS RESEARCH INSTITUTE, CHINESE ACADEMY OF AGRICULTURAL SCIENCES, Hubei (CN)

(72) Inventors: Qi Zhang, Hubei (CN); Peiwu Li, Hubei (CN); Yizhen Bai, Hubei (CN); Hui Li, Hubei (CN); Jun Jiang, Hubei (CN); Wen Zhang, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 1087 days.

(21) Appl. No.: 17/256,659

(22) PCT Filed: Nov. 29, 2019

(86) PCT No.: PCT/CN2019/121785
§ 371 (c)(1),
(2) Date: Dec. 29, 2020

(87) PCT Pub. No.: WO2020/114322
PCT Pub. Date: Jun. 11, 2020

(65) Prior Publication Data
US 2021/0189512 A1    Jun. 24, 2021

(30) Foreign Application Priority Data
Dec. 7, 2018   (CN) .......................... 201811491692.9

(51) Int. Cl.
*C12Q 1/6895*    (2018.01)
*C12Q 1/686*    (2018.01)

(52) U.S. Cl.
CPC .......... *C12Q 1/6895* (2013.01); *C12Q 1/686* (2013.01); *C12Q 2600/158* (2013.01)

(58) Field of Classification Search
None
See application file for complete search history.

(56) References Cited

U.S. PATENT DOCUMENTS 6,825,216 B1   11/2004   Trail et al.

FOREIGN PATENT DOCUMENTS

| CN | 101570792 | | 11/2009 | |
|---|---|---|---|---|
| CN | 105018621 | | 11/2015 | |
| CN | 109468367 | A * | 3/2019 | .......... C12Q 1/6851 |
| CN | 109557314 | | 4/2019 | |
| JP | 2006211936 | | 8/2006 | |

OTHER PUBLICATIONS

Hassan et al BVMJ. Dec. 2015. 29(2): 1-10 (Year: 2015).*
Abdel-Hadi et al (J Applied Microbiology. 2010. 109: 1914-1922 (Year: 2010).*
Iheanacho et al J. Microbiological Methods. Available online Dec. 27, 2013. 97: 63-67 (Year: 2013).*
Scherm et al. International J Food Microbiol. 2005. 98: 201-210 (Year: 2005).*
Zsuzsanna Mayer, et al., "Monitoring the Production of Aflatoxin B1 in Wheat by Measuring the Concentration of nor-1 mRNA." Applied And Environmental Microbiology, vol. 59, No. 2, Feb. 28, 2003, pp. 1154-1158.
Zsuzsanna Mayer, et al., "Quantification of the copy No. of nor-1, a Gene of the Aflatoxin Biosynthetic Pathway by real-time PCR, and its Correlation to the CFU of Aspergillus Flavus in Foods." International Journal of Food Microbiology, vol. 82, Dec. 31, 2003, pp. 143-151.
Yan Li, et al., "Research of Quantification of the Copy Number of nor-1, a Gene of the Aflatoxin Biosynthetic Pathway, in Fermented Bean Sauce by Real-time PCR." Food and Fermentation Industries, vol. 37, No. 11, Dec. 31, 2011, pp. 177-182.
Qin Wen-Yan, et al., "Multiplex PCR Detection of Aflatoxigenic Fungi Able to Contaminate Food and Feed." Mycosystema, vol. 26, No. 3, Dec. 31, 2007, pp. 448-454.
Yanru Wang, et al., "Isolation of Alpaca Anti-Idiotypic Heavy-Chain Single-Domain Antibody for the Aflatoxin Immunoassay." Analytical Chemistry, vol. 85, Sep. 2013, pp. 1-20.
"International Search Report (Form PCT/ISA/210)" of PCT/CN2019/121785, mailed on Mar. 13, 2020, with English translation thereof, pp. 1-6.

* cited by examiner

Primary Examiner — Carla J Myers
(74) Attorney, Agent, or Firm — JCIP GLOBAL INC.

(57) ABSTRACT

A method for identifying and evaluating toxigenic capability of an aflatoxigenic strain. A ratio of the aflatoxin yield to Nor-1 gene transcriptional quantity is determined to have high relative stability. An *Aspergillus flavus* strain toxigenic capability identification model is established, and thus a regression equation between the *Aspergillus flavus* toxigenic capability and the ratio AFT/Nor-1 of the aflatoxin yield to the Nor-1 gene transcriptional quantity is obtained.

4 Claims, 2 Drawing Sheets

Specification includes a Sequence Listing.

METHOD FOR IDENTIFYING AND EVALUATING TOXIGENIC CAPABILITY OF AFLATOXIGENIC STRAIN

CROSS-REFERENCE TO RELATED APPLICATION

This application is a 371 of international application of PCT application serial no. PCT/CN2019/121785, filed on Nov. 29, 2019, which claims the priority benefit of China application no. 201811491692.9, filed on Dec. 7, 2018. The entirety of each of the above mentioned patent applications is hereby incorporated by reference herein and made a part of this specification.

BACKGROUND

Field of the Disclosure

The disclosure belongs to the field of biology, and specifically relates to a method for identifying and evaluating the toxigenic capability of aflatoxigenic strain.

Description of Related Art

Aflatoxin is the most toxic mycotoxin found so far. Taking aflatoxin B1 as an example, its toxigenic capability is 10 times greater than that of potassium cyanide and 68 times greater than that of arsenic. Aflatoxin is classified as a Class I carcinogen by the International Cancer Organization. Aflatoxin can easily contaminate grain and oil products such as peanuts, corn, rice, etc., as well as many plant products such as walnuts, pistachios and Chinese medicinal materials. There have been many human and livestock poisoning incidents caused by aflatoxin in China and other countries. According to the latest report from the International Agency for Research on Cancer (IARC), about 500 million people in developing countries alone are at risk of exposure to aflatoxin. China is an area where there is a high-level of aflatoxin pollution. The results of the census conducted by the Ministry of Agriculture for many years show that the contamination of main agricultural products in China by aflatoxin is gradually increasing, and the content of toxins in highly contaminated areas exceeds the limit by hundreds of times. Although the highly-toxic mycotoxigenic strains account for less than 20%, they have become a major hidden danger that threatens the quality and safety of crop products.

Aflatoxin is mainly produced by fungi such as *Aspergillus flavus* and *Aspergillus parasiticus*. Studies have shown that the capabilities of different *Aspergillus flavus* strains in producing aflatoxin, that is, their toxigenic capability may be hundreds of times different. Strains with toxigenic capability are a major source of high contamination. However, so far there is a lack of effective method for efficiently identifying strains with toxigenic capability by using specificity. At present, there are mainly two methods for identifying the toxigenic capability of *Aspergillus flavus* strains: one is to evaluate the toxigenic capability of the strains by measuring the aflatoxin yield produced by the strains after a certain period of time of culturing the strain. For one thing, this type of method takes a long time because the strains must be isolated and then cultured, and then the evaluation is conducted by measuring the content of aflatoxin. For another, the biosynthesis of aflatoxin is affected by many and complex factors. Besides, the aflatoxin yield varies greatly from one batch to another batch of the same strains, and the toxigenic capability result is not suitable to be used to characterize the strain's inherent yield characteristics, which affects the accuracy and reliability of the identification and evaluation results of this method. Another type of method is to evaluate the toxigenic capability of strains by measuring the transcriptional quantity of genes related to toxigenic capability. There is literature regarding detection of Nor-1 gene for evaluating toxigenic capability. However, the disadvantage of this type of method is that in the natural state, there are defects in toxigenic genes other than the Nor-1 gene, which leads to the fact that even if the expression of the Nor-1 gene is detected, it does not produce aflatoxin by nature, and thus leading to false results of such methods.

Briefly, objectively and accurately identifying and evaluating the toxigenic capability of aflatoxigenic strain has been an unresolved problem to worldwide practitioners.

SUMMARY OF THE DISCLOSURE

In view of the deficiencies of the related art, the disclosure aims to provide a method for identifying and evaluating the toxigenic capability of aflatoxigenic strain.

In order to achieve the purpose of the disclosure, the technical solution adopted by the disclosure is:

A method for identifying and evaluating the toxigenic capability of aflatoxigenic strain includes the following steps, measuring the aflatoxin yield and Nor-1 gene transcriptional quantity of *Aspergillus flavus* strains to obtain the ratio of the aflatoxin yield to Nor-1 gene transcriptional quantity, identifying and evaluating the toxigenic capability of aflatoxigenic strain according to the ratio of the aflatoxin yield to Nor-1 gene transcriptional quantity.

According to the above solution, the method for measuring the aflatoxin yield includes the following steps: culturing the *Aspergillus flavus* strain, taking the spores of *Aspergillus flavus* for shaking culture, after the culture, filtering the filtrate, and measuring the concentration of aflatoxin in the filtrate.

According to the above solution, the medium used for culturing the *Aspergillus flavus* strain is CDA medium, and the culture conditions are: culture at 28° C. and 90% humidity for 10 days.

The medium used for shaking culture of the spores of *Aspergillus flavus* is a potato dextrose liquid medium, and the culture conditions are: shaking culture at 28° C. and 200 rpm for 96 hours.

According to the above solution, the immunoaffinity purification-high performance liquid chromatography standard method is adopted to measure the concentration of aflatoxin in the filtrate after shaking culture of the spores of *Aspergillus flavus*.

According to the above solution, the method for measuring the transcriptional quantity of the Nor-1 gene includes the following steps: culturing the *Aspergillus flavus* strain, taking the spores of *Aspergillus flavus* for shaking culture, after completion of the culture, filtering the hyphae of *Aspergillus flavus*, and obtaining the dried bacteria after drying, and then using the conventional Nor-1 gene transcriptional quantity measuring method to measure the Nor-1 gene transcriptional quantity in the dried bacteria.

According to the above solution, the aflatoxin yield and Nor-1 gene transcriptional quantity can also be obtained by the synchronization detection RT-PCR method. The specific steps include:

(1) Establishment of an S-type standard curve for quantifying aflatoxin: in the immune reaction stage, when the amount of aflatoxin monoclonal antibody coating is constant, use aflatoxin standard products of different concentrations to compete with phage surface displaying aflatoxin anti-idiotypic nano antibody to be bound to aflatoxin monoclonal antibody. After the immune competition reaction is over, the phage surface-displaying aflatoxin anti-idiotypic nano antibody bound to the aflatoxin monoclonal antibody is eluted. Aflatoxin standard products of different concentrations correspond to different amounts of eluted phage. The phage in the eluate will release the DNA molecules during the PCR heating process, and the released DNA molecules are used as the amplification targets in the RT-PCR reaction. Each of the eluate is subjected to the RT-PCR amplification reaction using the kit, and different Ct values are obtained after the amplification reaction is completed. The logarithm of the concentration of aflatoxin is the abscissa, and the Ct value is the ordinate, and regression analysis is performed to obtain the S-type standard curve for quantifying aflatoxin.

(2) Establishment of a RT-PCR standard curve for Nor-1 gene transcriptional quantity: serially dilute samples of known copy number of Nor-1 gene DNA fragment Tq-nor1 into different copy numbers, and then use the kit to perform RT-PCR amplification reaction to each copy number Tq-nor1 separately. Different Ct values are obtained after the amplification reaction. The logarithm of the copy number of Tq-nor1 is used as the abscissa and the Ct value is used as the ordinate to perform regression analysis, thereby obtaining standard curve for quantifying Nor-1 gene transcription.

(3) Culturing of *Aspergillus flavus* strain to obtain *Aspergillus* spores, taking the *Aspergillus flavus* spores for shaking culture. After the culture is completed, filter the strain culture solution and the fungus ball of *Aspergillus flavus*. After diluting the strain culture solution by a certain ratio, use it to replace the aflatoxin standard products in the immune reaction carried out in step (1) for the immune competition reaction. After the competitive reaction, the phage surface-displaying aflatoxin anti-idiotypic nano antibody bound to the aflatoxin monoclonal antibody is eluted, and the DNA molecules released by the phages in the eluate are used as the amplification template for quantifying aflatoxin in the synchronous RT-PCR amplification reaction. Additionally, after drying the fungus ball of *Aspergillus flavus*, the total RNA is extracted and reverse transcribed into cDNA, and the cDNA is diluted by a certain ratio and used as a template for the amplification of Nor-1 gene in the synchronous RT-PCR amplification reaction.

(4) Use the V2-5 bacteriophage and the cDNA as templates to perform the synchronous RT-PCR amplification reaction. After the amplification reaction, two Ct values are obtained, and the two Ct values are respectively substituted into the S-type standard curve for quantifying aflatoxin and standard curve for quantifying Nor-1 gene transcription, thereby making conversion to obtain the concentration of aflatoxin and Nor-1 gene transcriptional quantity, so as to determine the ratio of aflatoxin yield to Nor-1 gene transcriptional quantity.

According to the above solution, the phage surface-displaying aflatoxin anti-idiotypic nano antibody is phage VHH 2-5, and the aflatoxin monoclonal antibody is the aflatoxin monoclonal antibody 1C11.

According to the above solution, in the reaction system of the synchronous RT-PCR amplification reaction, the final concentration of the upstream and downstream primers: Ph-F, Ph-R, Tq-nor1-F, and Tq-nor1-R is 300 to 400 nM; fluorescent probe: the final concentration of Ph-probe and Tq-probe is 200 to 400 nM; final dosage of DNA polymerase: 0.5 U to 1.0 U; final concentration of $MgCl_2$: 1 mM to 2 mM; final concentration of dNTPs: 200 uM to 400 uM.

According to the above solution, the nucleotide sequence of the upstream primer Ph-F is shown in SEQ ID NO. 1; the nucleotide sequence of the downstream primer Ph-R is shown in SEQ ID NO. 2; the nucleotide sequence of fluorescent probe Ph-probe is shown in SEQ ID NO. 3; the nucleotide sequence of the upstream primer Tq-nor1-F is shown in SEQ ID NO. 4; the nucleotide sequence of the downstream primer Tq-nor1-R is shown in SEQ ID NO. 5; the nucleotide sequence of fluorescent probe Tq-probe is shown in SEQ ID NO. 6.

According to the above solution, the reaction system of the synchronous RT-PCR amplification reaction includes: universal probe qPCR master mix 5 μL, Ph-F 0.1 μL, Ph-R 0.1 μL, Ph-probe 0.1 μL, phage template 2 μL, Tq-nor1-F 0.1 μL, Tq-nor1-R 0.1 μL, Tq-probe 0.1 μL, Nor-1 gene template 1 μL, DNA polymerase 0.2 μL, $MgCl_2$ 0.84, dNTPs 0.2 μL, add $H_2O$ to make it up to 10 μL.

According to the above solution, the conditions of the RT-PCR synchronous amplification reaction are 95° C., 5 min; 95° C., 10 s, 60° C., 30 s, 40 cycles.

According to the above solution, the concentration range of aflatoxin in the S-type standard curve for quantifying aflatoxin is 33.33 ng/ml to 1.69 pg/mL, and the lowest detection line LOD of aflatoxin is 0.018 ng/ml. In the standard curve for quantifying Nor-1 gene transcription, the copy number of Nor-1 gene ranges from 102 to 108

According to the above solution, the toxigenic capability of the aflatoxigenic strain is defined as Y, and the ratio of aflatoxin yield to Nor-1 gene transcriptional quantity (AFT/Nor-1) is defined as X. The formula for identifying toxigenic capability of *Aspergillus flavus* is $Y=10.14X-16.20$. For highly toxigenic strain, the toxigenic capability is >150 ng/mL; the medium toxigenic capability: 50<the toxigenic capability<150 ng/mL; the low toxigenic capability: the toxigenic capability<50 ng/mL; no toxin: 0. Substitute the above values into the formula to calculate the identification range of toxigenic capability: AFT/Nor-1>16.4, which indicates a highly toxigenic strain; 6.5<AFT/Nor-1<16.4, which indicates a medium toxigenic strain; 0<AFT/Nor-1<6.5, which indicates a low toxigenic strain; AFT/Nor-1=0, which indicates a non-toxigenic strain.

The advantageous effect of the disclosure is as follows.

(1) The research of the disclosure has proved that the ratio of the aflatoxin yield to the Nor-1 gene transcriptional quantity is of high relative stability. By establishing the identification model of the toxigenic capability of *Aspergillus flavus* strains, the regression equation for the ratio of toxigenic capability of *Aspergillus flavus* and aflatoxin yield to Nor-1 gene transcriptional quantity (AFT/Nor-1) can be obtained. By determining the AFT/Nor-1 ratio, it is possible to realize fast and accurate identification and evaluation of toxigenic capability of *Aspergillus flavus* strains, and which is of great significance to the early warning and prevention and controlling of aflatoxin pollution.

(2) The disclosure establishes a synchronous RT-PCR detection method for synchronously detecting the toxigenic capability of *Aspergillus flavus* strains and the Nor-1 gene transcriptional quantity. There is a good linear relationship between the toxigenic capability of *Aspergillus flavus* strains and Nor-1 gene transcriptional quantity obtained by using the synchronous detection RT-PCR method of the disclosure and the aflatoxin quantified through HPLC as well as the Nor-1 gene transcriptional quantity quantified through Nanodrop. Therefore, the result obtained for the ratio of AFT/Nor-1 (toxigenic capability of *Aspergillus flavus* strain/Nor-1 gene transcriptional quantity) obtained based on the synchronous detection RT-PCR method is reliable and accurate, and can be used as an identification index to determine the toxigenic capability of *Aspergillus flavus* strain.

(3) In the synchronous detection RT-PCR method for toxigenic capability of *Aspergillus flavus* strain and Nor-1 gene transcriptional quantity described in the disclosure, the required amount of reagents is less, and the cost is lower, and therefore high-throughput detection can be achieved. The synchronous detection RT-PCR method simplifies the analysis mode, optimizes the experimental process and structure, and provides a detection platform and theoretical basis for the synchronous analysis of aflatoxin and other small molecules in its synthesis pathway.

DESCRIPTION OF EMBODIMENTS

Figure 1:
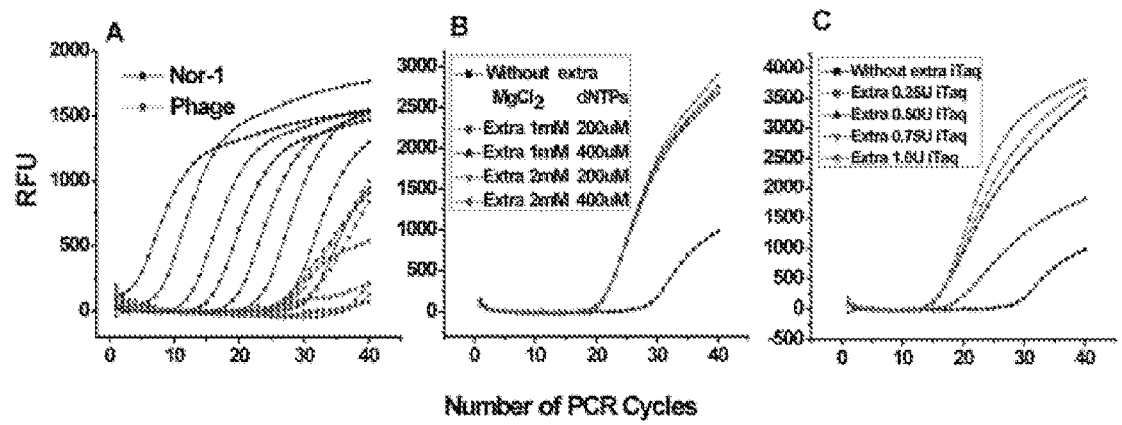
FIG. 1 shows the optimization of the concentration of DNA polymerase, dNTPs and $MgCl_2$ in the synchronous RT-PCR reaction.

In order to make the disclosure more comprehensible, the content of the disclosure will be further clarified below in conjunction with the embodiments, but the content of the disclosure is not limited to the following embodiments.

Embodiment 1

1. The Study Proved that the Ratio of Aflatoxin Yield to Nor-1 Gene Transcriptional Quantity is of High Relative Stability.

Weigh 1 g of $NaNO_3$, 1 g of $K_2HPO_4$, 0.5 g of $MgSO_4 \cdot 7H_2O$, 0.5 g of KCl, 0.01 g of $FeSO_4$, 30 g of glucose and 20 g of agar powder. Dilute them with deionized water to a total volume of 1000 ml, and sterilize them with high temperature steam at 121° C. for 30 min, so as to prepare a CDA medium. *Aspergillus flavus* strain is cultured with the CDA solid medium at 28° C. and 90% humidity for 10 days, and then the culture plate is washed with 20% Tween-20 to obtain a solution of *Aspergillus flavus* spores. Use the hemocytometer counting method, the *Aspergillus flavus* spore solution is shaken evenly with a vortex oscillator, and the *Aspergillus flavus* spore solution is counted microscopically with a microscope.

Put 15 mL of potato dextrose liquid medium in a 50 mL Erlenmeyer flask, autoclave the potato dextrose liquid medium at 121° C. for 30 min. Thereafter, based on the counting results, add the *Aspergillus flavus* spore solution until the final concentration is $1 \times 10^5$ spores per ml, and culture with shaking at 28° C. and 200 rpm for 96 h. Filter the culture broth with double-layer filter paper to obtain the filtrate (preserved for later use) and the fungus ball of *Aspergillus flavus*. For the fungus ball of *Aspergillus flavus*, squeeze the excess water with filter paper, and dry it in an oven at 65° C. for 12 hours to obtain dried bacteria. After cooling it to room temperature, store it at −70° C. for later use. The filtrate obtained through filtering is stored at 4° C. for later use.

The immunoaffinity purification-high performance liquid chromatography standard method is adopted to measure the concentration of aflatoxin in the filtrate (stored for later use as described above) after shaking culture of the spores of *Aspergillus flavus*, and then the conventional Nor-1 gene transcriptional quantity measuring method is adopted to measure the Nor-1 gene transcriptional quantity in the dried bacteria stored for later use.

Adopt the same operation as described above, seven *Aspergillus flavus* strains are cultured at different time periods before and after two batches are tested. The measuring results are shown in Table 1.

TABLE 1

The measuring result of aflatoxin yield from Aspergillus flavus strains and relative amount of Nor-1 gene transcription

| | The culture measurement results for first batch | | | The culture measurement results for second batch | | |
|---|---|---|---|---|---|---|
| strains | aflatoxin ng/mL | relative amount of Nor-1 | [AFT]/ [Nor-1] | aflatoxin ng/mL | relative amount of Nor-1 | [AFT]/ [Nor-1] |
| 1 | 204.2 | 10.6 | 19.3 | 172.3 | 8.7 | 19.8 |
| 2 | 158.3 | 9.1 | 17.4 | 143.6 | 8.1 | 17.7 |
| 3 | 141.3 | 9.6 | 14.7 | 152.6 | 10.8 | 14.1 |
| 4 | 53.2 | 8.6 | 6.2 | 86.5 | 12.9 | 6.7 |
| 5 | 19.7 | 8.3 | 2.4 | 22.7 | 8.7 | 2.6 |
| 6 | 1.7 | 6.7 | 0.3 | 0.9 | 3.4 | 0.3 |
| 7 | 0 | 5.6 | 0 | 0 | 4.1 | 0 |

According to the measuring results in Table 1, there is a big difference between the concentration of aflatoxin in the two batches, and therefore the aflatoxin yield alone cannot serve to evaluate of the toxigenic capability of *Aspergillus flavus* strains. In some cases where the relative amount of Nor-1 gene transcription to *Aspergillus flavus* strains is high, the toxigenic capability is unexpectedly low. In addition, non-toxigenic strains can also transcribe the Nor-1 gene, and therefore the Nor-1 gene alone cannot serve to evaluate the toxigenic capability of *Aspergillus flavus* strains either. Surprisingly, in Table 1, in the ratio obtained by dividing the concentration of aflatoxin by the relative amount of Nor-1 gene transcription, that is, the [AFT]/[Nor-1] value in Table 1, a high regularity is found. Not only that the orders of the toxigenic capability of the 7 strains obtained from the two culture batches are consistent, but also the [AFT]/[Nor-1] value of each strain is relatively stable, and thus qualifying to evaluate the toxigenic capability of *Aspergillus flavus* strains.

It can be seen from the data in Table 1 that, if the ratio of the concentration of aflatoxin to the relative amount of Nor-1 gene transcription is adopted to evaluate the toxigenic capability of *Aspergillus flavus* strains, the accuracy and reliability of such as approach are significantly better than the approach of using the concentration of aflatoxin alone of the approach of using relative amount of Nor-1 gene transcription alone.

Embodiment 2 Establishment of Synchronous Detection RT-PCR Method for Aflatoxin Yield and Nor-1 Gene Transcriptional Quantity Utilize the known phage VHH 2-5 surface-displaying aflatoxin anti-idiotypic nano antibody and Nor-1 gene DNA fragment Tq-nor1 to establish synchronous detection RT-PCR method for aflatoxin yield and Nor-1 gene transcriptional quantity. The above detection result is used as the scientific basis for identifying and evaluating the toxigenic capability of *Aspergillus flavus* strains, which provides support for the method of rapid identification and evaluation of the toxigenic capability of *Aspergillus flavus* strains. The specific steps are as follows.

The phage VHH 2-5 surface-displaying aflatoxin anti-idiotypic nano antibody is developed by the Quality Inspection Center of Oil Crop Research Institute, Chinese Academy of Agricultural Sciences, and has been published in the journal "Yanru Wang; Peiwu Li; Zuzana Majkova; Candace RS Bever; Hee Joo Kim; Qi Zhang; Julie E. Dechant; Shirley J. Gee; Bruce D. Hammock; Isolation of Alpaca Anti-Idiotypic Heavy-Chain Single-Domain Antibody for the Aflatoxin Immunoassay; Analytical Chemistry, 2013, 8298-8303". The phage used in this example is stored in *E. coli* ER2738 in advance in the laboratory and obtained by amplification. The amplification method is as follows:

Pick a single colony randomly from the ER2738 single colony plate holding the nano antibody phage VHH 2-5, inoculate it into a liquid medium containing 1 mL of SB-ampicillin, and incubate overnight at 225 rpm in a constant temperature shaker at 37° C. Add the above overnight culture broth to 100 mL of SB-ampicillin liquid medium at 225 rpm and 37° C. and culture it to $OD_{600}$=0.5-0.6. Add 1.5 ml of M13KO7 helper phage (titer $1\times10^{11}$-$1\times10^{12}$ pfu/mL) to the cultured bacteria solution, and let it stand at 37° C. for 30 min. Add kanamycin with a final concentration of 70 μg/mL to the broth at 37° C. and 225 rpm, and shake culture it overnight. Centrifuge the broth cultured overnight at 4° C. and 10000 rpm for 15 minutes, take the supernatant, and transfer it to a clean centrifuge bottle. Add ¼ volume of PEG/NaCl and let it stand on ice for 2 hours. Centrifuge it at 10000 rpm for 30 minutes at 4° C., re-suspend it with 2 mL of 0.5% BSA/PBS, and then centrifuge it at 12000 rpm for 5 min. Take the supernatant, filter the supernatant with a 0.22 μm filter and mix it with an equal volume of sterile glycerin, aliquot and measure the titer. The titer measuring method is as follows:

Randomly pick a single colony from the ER2738 single colony plate, inoculate it into a LB liquid medium containing 0.04 mg/mL of tetracycline, culture it overnight in a constant temperature shaker at 37° C. at 225 rpm. Take 20 μL of the above broth that is cultured overnight and add it to 2 mL SB medium. Incubate it at 225 rpm and 37° C. to $OD_{600}\approx1$. Use LB liquid medium to gradually dilute the phage that needs to be tested for titer. Take 10 μL of each dilution and add it to 100 μL of ER2738 broth with $OD_{600}\approx1$, and let it stand at 37° C. for 20 minutes. Make the phage infect *E. coli*; spread the infected *E. coli* broth on the LB-ampicillin plate, put it upright in a constant temperature incubator at 37° C. for 30 minutes, and then invert the culture overnight. Select about 100 of single colonies for plate counting, and calculate the titer of phage according to the following formula:

$$\frac{\text{Number of single colony}\times\text{ratio for dilution}\times1000\ \mu\text{l/ml}}{\text{Add volume of phage }(\mu\text{l})}$$

The method for obtaining the Nor-1 gene DNA fragment Tq-nor1: Put 15 mL of potato dextrose liquid medium in a 50 mL Erlenmeyer flask, autoclave it at 121° C. for 30 min, and add the spore solution of No. N73 *Aspergillus flavus* until the final concentration is $1\times10^5$ $ml^{-1}$. After shaking culture at 28° C., 200 rpm for 96 h, use double-layer filter paper to squeeze out the fungus ball culture solution, dried it at 65° C. for 12 h, quick-frozen it with liquid nitrogen, and ground it into powder. Accurately weigh 200 mg of hyphal powder, use the DNA extraction kit (DNeasy Plant Mini Kit) to extract the genomic DNA of strain N73 according to the kit instructions. Use the following primers (the sequence of Nor1-F is shown in SEQ ID No.7; the sequence of Nor1-R is shown in SEQ ID NO.8) to amplify the nor Nor-1 gene fragment product with a size of 400 bp, and use E.Z.N.A.T.M (OMEGA) gel extract kit to purify the DNA fragment with a size of 400 bp according to the instructions to obtain Tq-nor1.

```
Nor1-F:
                                        (SEQ ID NO. 7)
5'-ACCGCTACGCCGGCACTCTCGGCAC-3';

Nor1-R:
                                        (SEQ ID NO. 8)
5'-GTTGGCCGCCAGCTTCGACACTCCG-3'.
```

1. Establishment of Synchronous Detection RT-PCR Method for Aflatoxin Yield and Nor-1 Gene Transcriptional Quantity 1. Design of Primers and Probe Sequences for Synchronous Detection RT-PCR for Aflatoxin Yield and Nor-1 Gene Transcriptional Quantity The DNA fragment Tq-nor1 of the DNA fragment and Nor-1 gene released by the phage VHH 2-5 surface-displaying aflatoxin anti-idiotypic nano antibody is adopted as the template for RT-PCR synchronous amplification. Determine the ratio of aflatoxin yield to Nor-1 gene transcriptional quantity through synchronous RT-PCR amplification results.

Encoding the sequence of nano antibody and Nor-1 gene sequence, the sequence of the upstream and downstream primers (Ph-F, Ph-R) of aflatoxin and the probe (Ph-probe), and the sequence of upstream and downstream primers (Tq-nor1-F, Tq-nor1-R) of Tq-nor-1 and the probe (Tq-probe) according to the phage VHH 2-5 surface-displaying aflatoxin anti-idiotypic nano antibody. Then use Oligo7.0 primer analysis software to perform verification according to the design principles and guidelines for primers and probes in the double RT-PCR reaction.

Primer and probe verification principle: The TM value of all primers should be set to the same or similar level, and the TM value of all probes should be as similar as possible and greater than the TM value of the primer by about 5° C. to 10° C. Because the reaction is a synchronous reaction of the same system, ensure that all primers and probes are not easily formed into dimers. Perform BLAST search to ensure that primers and probes are specific to the intended target.

It is determined that the following primers and probe sequences meet the above principles and requirements, as summarized in Table 2.

TABLE 2

Double fluorescent quantitative RT-PCR primers and probe sequences

| Primers/ Probes | Sequence (5' to 3') | Tm (° C.) | Length (bp) | Target gene |
|---|---|---|---|---|
| Ph-F | GTGGTAGCACAAACTATG (SEQ ID NO. 1) | 49.5 | 131 | VHH 2-5 |
| Ph-R | GGCTGCACAGTAATAAAC (SEQ ID NO. 2) | 50.2 | | Phage |

TABLE 2-continued Double fluorescent quantitative RT-PCR primers and probe sequences

| Primers/Probes | Sequence (5' to 3') | Tm (° C.) | Length (bp) | Target gene |
|---|---|---|---|---|
| Ph-probe | FAM-CCGATTCACCATCTCCAGAGACA-BHQ1 (SEQ ID NO. 3) | 58.2 | | |
| Tq-nor1-F | GTCCAAGCAACAGGCCAAGT (SEQ ID NO. 4) | 57.4 | 66 | Nor-1 |
| Tq-nor1-R | TCGTGCATGTTGGTGATGGT (SEQ ID NO. 5) | 55.4 | | |
| Tq-probe | TET-TGTCTTGATCGGCGCCCG-BHQ1 (SEQ ID NO. 6) | 62.2 | | |

2. The Reaction Parameters of the Synchronous RT-PCR Detection Method for the Aflatoxin Yield and Nor-1 Gene Transcriptional Quantity Synchronous RT-PCR reaction parameters are different from RT-PCR amplified through single gene, because it is necessary to carefully consider the interference between the reaction systems. First, RT-PCR amplify two single-stranded-specific DNA fragment of aflatoxin anti-idiotypic nanobody phage and DNA fragment of Nor-1 gene. The reaction components are directly mixed without adding other components, and then perform double RT-PCR reaction, the result is shown in A of FIG. 1. From the figure it can be seen that the amplification of VHH 2-5 phage DNA molecules is significantly inhibited. In a double RT-PCR reaction, the amplification efficiency and target sequence of different amplified products may be different. The amplification of samples with low amplification efficiency or low-abundance target sequences may be inhibited by highly amplified sample or target sequence with higher abundance.

For this reason, the disclosure optimizes the RT-PCR reaction conditions of the synchronous detection method for aflatoxin yield and Nor-1 gene transcriptional quantity. In the disclosure, the concentrations of DNA polymerase, $MgCl_2$ and dNTPs are optimized. The result shown in B of FIG. 1 shows that, when the concentration of VHH 2-5 phage is $10^6$ pfu/mL, the loop threshold Ct moves forward after dNTPs and $MgCl_2$ are added additionally, and an amplification curve appears at an earlier loop cycle. Therefore, it is shown that the amplification of DNA molecules of VHH 2-5 phage is improved. C of FIG. 1 shows that, when the DNA polymerase is increased from 0.25 U to 1.0 U, the amplification efficiency of the phage is also significantly improved. Therefore, based on the principle that the earlier the threshold loop Ct appears, the closer the amplification curve is to the S-shape in the exponential phase, the preferred dosage range of DNA polymerase, $MgCl_2$ and dNTPs of the disclosure is:

DNA polymerase: 0.5 U to 1.0 U; $MgCl_2$: 1 mM to 2 mM; dNTPs: 200 uM to 400 uM.

According to the above research results, the disclosure provides the final optimized amplification reaction parameters, as shown in Table 3.

TABLE 3

RT-PCR reaction parameters of synchronous detection method for aflatoxin and Nor-1 gene transcriptional quantity

| Ingredient | Volume | Final concentration | Template | Reaction conditions |
|---|---|---|---|---|
| Universal Probes supermix | 5 ul | | | 95° C. 5 min, 1 cycle |
| Ph-F | 0.1 ul | 400 nM | VHH 2-5 | 95° C. 10 s, |
| Ph-R | 0.1 ul | 400 nM | Phage | 60° C. 30 s, |
| Ph-probe | 0.1 ul | 200 nM | | 40 cycle |
| Phage | 2 ul | | | |
| Tq-nor1-F | 0.1 ul | 400 nM | Nor-1 | |
| Tq-nor1-R | 0.1 ul | 400 nM | | |
| Tq-probe | 0.1 ul | 200 nM | | |
| Nor-1 | 1 ul | | | |
| iTaq | 0.2 ul | 1.0 U | | |
| $MgCl_2$ | 0.8 ul | 2 mM | | |
| dNTPs | 0.2 ul | 200 uM | | |
| $H_2O$ | Add water to make it up to 10 ul | | | |

Figure 2:
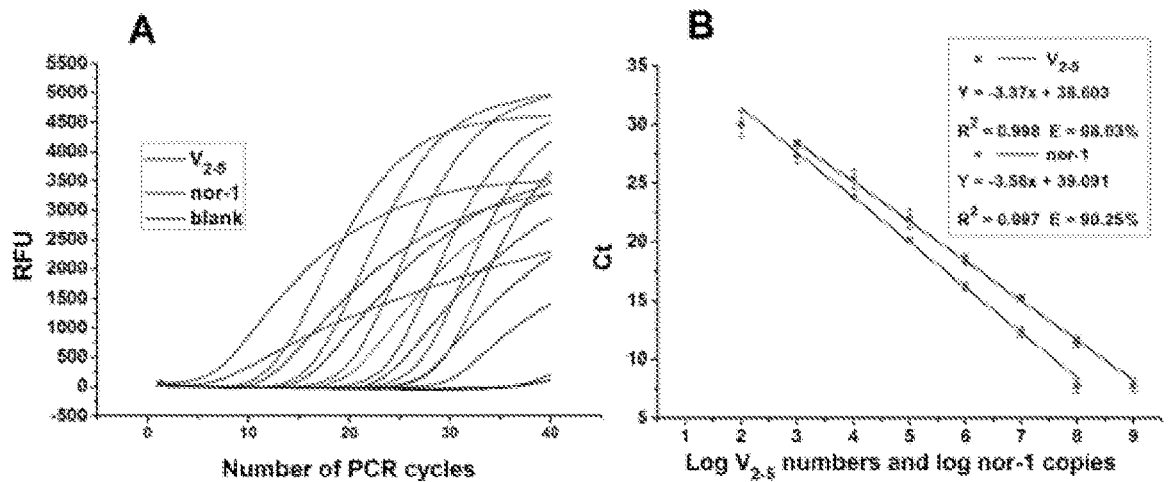
FIG. 2 shows the evaluation of synchronous RT-PCR amplification efficiency.

3. Amplification Efficiency of Synchronous Detection RT-PCR Method for Aflatoxin Yield and Nor-1 Gene Transcriptional Quantity The synchronous RT-PCR amplification results of serially diluted phage and serially diluted Nor-1 are shown in the synchronous RT-PCR amplification curve (RFU, relative fluorescent unit), as shown in A of FIG. 2. B of FIG. 2 is the standard curve of amplification efficiency obtained from the amplification curve. The slope of the standard curve of the amplification efficiency of phage VHH 2-5 is −3.37. Calculate by using the calculation formula of amplification efficiency E ($E = [10^{1/-slope} - 1] \times 100\%$), when the amplification efficiency E is 98.03%, the detectable concentration range of VHH 2-5 phage is $10^9$ to $10^3$ pfu/mL. When the copy number of DNA fragment Tq-nor1 of the Nor-1 gene is $10^2$ to $10^8$ copies, the amplification efficiency of the Nor-1 gene is 90.25% by analogy. The amplification efficiency E meets the required range of 90% to 105%, and the correlation coefficient R2 of the amplification efficiency standard curve is >0.99. Therefore, the optimized synchronous RT-PCR system can be used for the synchronous and efficient amplification of VHH 2-5 phage and Nor-1 gene.

2. Establishment of Quantitative Standard Curve and Evaluation of Synchronous RT-PCR Method
1. S-type Standard Curve for Quantifying Aflatoxin
1.1 Immune Response (1) Coating: Use PBS to dilute the commercially available aflatoxin monoclonal antibody 1C11 (secreted by hybridoma cell strain 1C11 with preservation number CCTCC NO: C201013, patent application number is CN201010245095.5, specific reports thereof are available) to 1.0 μg/mL. Use micropipette to add it to a 96-well microplate, 100 μL per well, incubate it overnight at 4° C. (≈12 h), wash the plate 3 times with PBST; block it: block each well with blocking solution, 300 μL per well, incubate it at 37° C. for 45 min, wash the plate 3 times with PB ST.

(2) Blocking: Block with blocking solution, 300 μL per well, incubate it at 37° C. for 45 min, wash the plate 3 times with PBST.

(3) Competition: Dilute the aflatoxin B1 standard product with 100% pure methanol to a concentration of 200 ng/mL, then dilute the standard solution of aflatoxin B1 with a 3-fold gradient of 10% (v/v) methanol/PBS, such that the concentration range is 33.33 ng/mL to 1.69 pg/mL. Then mix VHH 2-5 phage with known concentration ($1.0 \times 10^{10}$ cfu/mL) with aflatoxin B1 of 50 μL series concentration, add 10 μL of the mixture to 96-well microtiter plate. After incubation at 37° C. for 1 h, wash the plate with PBST for 10 times.

(4) Elution: Inject 90 μL of phage eluate into each well, leave it in a warm bath at 37° C. for 15 minutes, gently blow and hit it with a micropipette and transfer the eluate containing phagemid.

(5) Neutralization: Mix 90 μL of the removed solution with 10 μL of the neutralization solution to make the mixture neutral—the volume of the neutralization solution added is adjusted according to the actual pH value of the eluent and neutralization solution to ensure that the mixture is neutral.

1.2 Establish a standard curve: In the immune reaction stage, under the condition that the coating amount of aflatoxin monoclonal antibody 1C11 is fixed, aflatoxin of different concentrations will compete with VHH 2-5 phage of different amounts to bind to 1C11. The greater the concentration of aflatoxin, the smaller the chance for phage to bind to 1C11 and the lower the binding amount. After the immune response is over, the phage bound to 1C11 will be eluted. The number of phages in the eluate is related to the concentration of aflatoxin. The phagemid in the eluate will release DNA molecules during the heating process of the PCR reaction. The released DNA molecules are used as the amplification target in the RT-PCR reaction. After the amplification reaction, the fluorescence quantification system software will provide the Ct values of amplification of phages of different amounts in different eluates corresponding to aflatoxin of different amounts. The Ct values obtained by serially diluting aflatoxin of different concentrations (33.33 ng/ml to 1.69 pg/mL) to the logarithm of aflatoxin concentration is subjected to four-parameter logistic regression by using Origin Pro 8.0 software, and the result is used as the S-type standard curve for the quantification of aflatoxin, as shown in A of FIG. 3.

2. Establishment of standard curve for quantifying Nor-1 gene transcription

An *Aspergillus flavus* strain is taken. In this example, the *Aspergillus flavus* strain N73 preserved by the research center is used, which is a highly toxigenic strain and is used in the preparation of Tq-nor1 in this study. For other *Aspergillus flavus* strains, it is possible to use "method for obtaining DNA fragment Tq-nor1 of Nor-1 gene" described above to amplify DNA fragment Tq-nor1 with a size of 400 bp. Both of them can be used as candidate strains for establishing the standard curve for quantifying Nor-1 gene transcription. After using spectrophotometer (NanoDrop 2000, Thermo Scientific, U.S.A.) to detect the concentration of Tq-nor1, calculate the copy number of Tq-nor1. Tq-nor1 is serially diluted ($10^2$ to $10^8$ copies) as a sample with known amount, and then subjected to RT-PCR amplification. Use Origin Pro 8.0 software, wherein the logarithm value of the Tq-nor1 standard sample serial copy number is the abscissa and the Ct value is the ordinate for performing regression analysis. B of FIG. 3 shows the standard curve for quantifying Nor-1 gene transcription.

Figure 3:
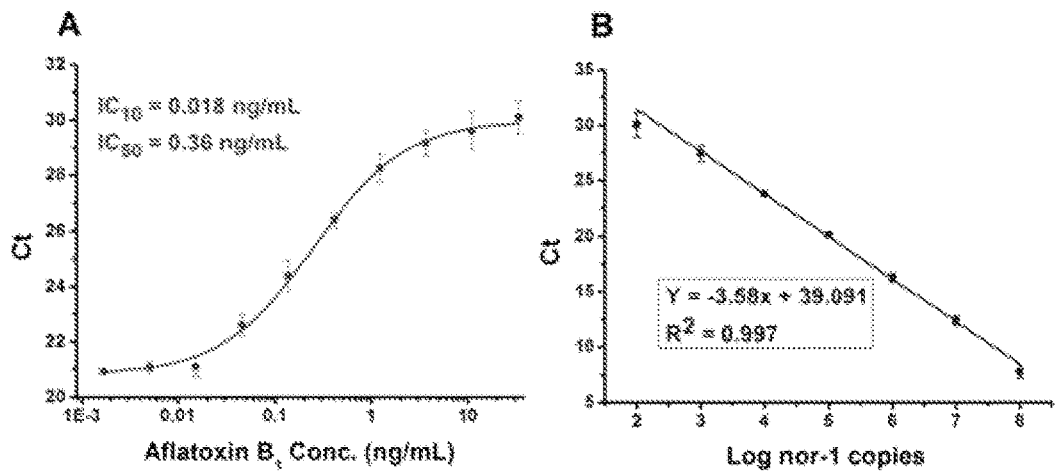
FIG. 3 is a quantitative standard curve for quantifying aflatoxin B1 and Nor-1 gene transcription thorough synchronous RT-PCR method.

The standard curve for quantifying aflatoxin is shown in A of FIG. 3. It can be seen from the figure that the detection limit LOD (expressed by IC10) for quantifying aflatoxin B1 through synchronous RT-PCR is 0.018 ng/mL. Therefore, the established RT-PCR quantitative detection of aflatoxin B1 is of high sensitivity. In addition, B of FIG. 3 reveals that synchronous RT-PCR can quantify Nor-1 gene copy numbers to range from $10^2$ to $10^8$, which fully proves that the established synchronous RT-PCR has prominent advantages in the low-level absolute quantification of Nor-1 gene.

3. Measurement of Cross-Reactivity of Aflatoxin in Synchronous RT-PCR Detection

Figure 4:
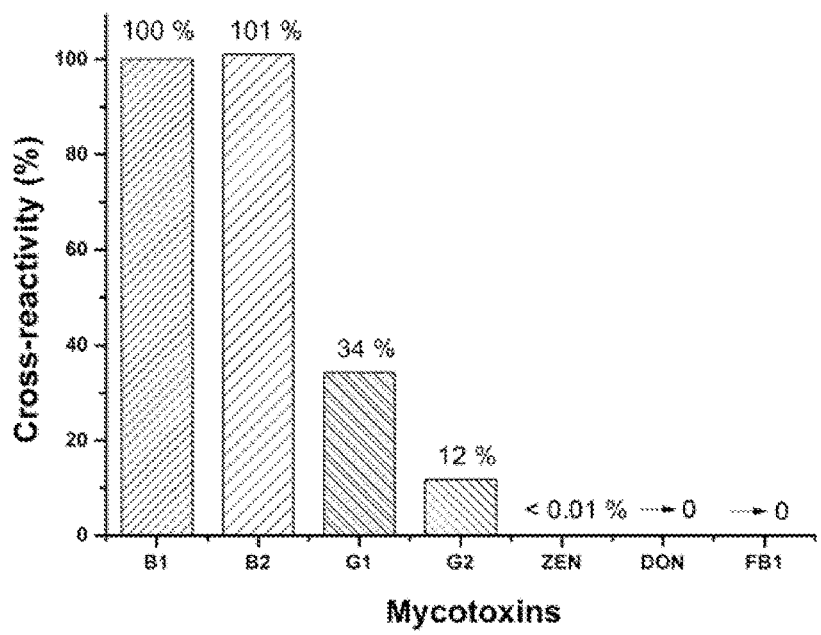
FIG. 4 shows the cross-reactivity of synchronous RT-PCR quantification to aflatoxin B1, B2, G1, G2, ZEN, DON, FB1.

Aflatoxin B2, G1, G2, Zearalenone (ZEN), Deoxynivalenol (DON), Fumonisin (FB1) standard products are diluted to a series of concentrations. After they compete with phage VHH 2-5 in the competitive immune reaction, the phage bound to the monoclonal antibody 1C11 at bottom of the microplate is eluted to undergo RT-PCR synchronous amplification with Tq-nor1. The Ct value obtained by the amplification corresponds to the logarithmic value of the different concentration of toxin to be used as the standard curve. Calculate the $IC_{50}$ value, and calculate the cross-reactivity according to the cross-reactivity calculation formula % $CR=(IC_{50\ AFB1}/IC_{50\ analyte})\times100$. As shown in FIG. 4, the cross-reactivity for aflatoxin B1, B2, G1, and G2 are 100%, 101%, 34%, and 12%, respectively. It can be seen that the method can realize the measurement of the total amount of aflatoxin. Specifically, the cross-reactivity of aflatoxin G1 and G2 are 34% and 12%, respectively, but which does not affect the application of the method in identifying the toxigenic capability of *Aspergillus flavus* because the *Aspergillus flavus* strains only produce the group B aflatoxin. The cross-reactivity of aflatoxin B2 is 101%. The established RT-PCR method for quantifying aflatoxin B2 is of higher sensitivity, which at a certain level improves the reliability of the established RT-PCR method for identifying toxigenic capability of *Aspergillus flavus* for the reason that *Aspergillus flavus* strains can produce aflatoxin B1 as well as aflatoxin B2. Therefore, using the established RT-PCR to identify the toxigenic capability of *Aspergillus flavus* strains is an assessment of the comprehensive yield of B1 and B2.

4. Verification of Addition Recovery in Synchronous RT-PCR

Aflatoxin B1 standard product and DNA fragment Tq-nor-1 of Nor-1 gene are simultaneously added to a 2 mL blank PDB medium. Shake and mix them well, and after mixing evenly, place the mixed solution at 4° C. and avoid light for 4 days. After 4 days, the mixture is diluted by 20 times, and the contents of aflatoxin B1 and Tq-nor-1 in the mixture are synchronously detected by RT-PCR. Set 3 replicates in the group of the same day, and set 3 replicates between groups of different days. The results of addition recovery are shown in Table 4:

TABLE 4

Measurement of Addition Recovery

| Experiment type | aflatoxin B 1 | | | | Tq-nor-1 | | | |
|---|---|---|---|---|---|---|---|---|
| | Amount of addition (ng/mL) | Mean ± SD | Average recovery rate (%) | CV (%) | Amount of addition log (copy number) | Mean ± SD | Average recovery rate (%) | CV (%) |
| Intra-group a experiment | 10 | 8.84 ± 0.30 | 88.37 | 3.43 | 9 | 8.84 ± 0.13 | 98.17 | 1.50 |
| | 100 | 92.10 ± 6.12 | 92.10 | 6.65 | 7 | 6.79 ± 0.29 | 97.00 | 4.33 |

TABLE 4-continued

Measurement of Addition Recovery

| | aflatoxin B 1 | | | Tq-nor-1 | | | |
|---|---|---|---|---|---|---|---|
| Experiment type | Amount of addition (ng/mL) | Mean ± SD | Average recovery rate (%) | CV (%) | Amount of addition log (copy number) | Mean ± SD | Average recovery rate (%) | CV (%) |
| (n = 3) | 200 | 206.20 ± 5.50 | 103.10 | 2.67 | 5 | 4.43 ± 0.22 | 88.61 | 4.89 |
| Inter-group b | 10 | 9.15 ± 0.88 | 91.50 | 9.64 | 9 | 8.79 ± 0.18 | 97.70 | 2.05 |
| experiment | 100 | 92.91 ± 8.20 | 92.91 | 8.83 | 7 | 6.49 ± 0.64 | 92.80 | 9.78 |
| (n = 3) | 200 | 198.21 ± 14.93 | 99.11 | 7.53 | 5 | 4.31 ± 0.39 | 86.18 | 9.04 |

The addition recovery rate of aflatoxin B1 is 88.37% to 103.10%, and the addition recovery rate of DNA fragment Tq-nor-1 of Nor-1 gene is 86.18% to 98.17%. This result shows that the established synchronous RT-PCR has reliable repeatability and reproducibility in actual sample detection and analysis.

5. Apply synchronous RT-PCR method to quantify the expression level of toxigenic capability of *Aspergillus flavus* strains and Nor-1 gene In this study, 17 *Aspergillus flavus* strains with different toxigenic capability are selected. Put 15 mL potato dextrose liquid medium in a 50 mL Erlenmeyer flask, autoclave it at 121° C. for 30 min, add the *Aspergillus flavus* spore solution until the final concentration is $1 \times 10^5$ ml$^{-1}$. After shaking culture at 28° C. and 200 rpm for 96 h, filter the culture broth with double-layer filter paper to obtain the strain culture broth and *Aspergillus flavus* fungus ball. Use filter paper to squeeze the excess water out of the *Aspergillus flavus* fungus ball and dry it for 12 hours at 65° C. by using an oven, cool it to room temperature, grind it into powder with liquid nitrogen, and accurately weigh 0.20 mg of fungus powder per sample. Follow the RNA extraction kit (RNeasy Plant Mini Kit) instructions for performing total RNA extraction. Then use QuantiTect reverse transcription kit to synthesize cDNA. The cDNA solution is diluted by 100 to 1000 times and replace Tq-nor1 in the synchronous RT-PCR amplification system, and used as one of the amplification templates to perform synchronous RT-PCR amplification to measure the Nor-1 gene transcriptional quantity. After the strain culture medium is diluted by 10 times with 10% (w/v) BSA/PBS, it replaces the aflatoxin standard product in the immune reaction to participate in the immune competition reaction. After the competition reaction, the phagemid in the eluate is used as another template of the synchronous RT-PCR amplification system, and synchronous RT-PCR amplification is performed to measure the toxigenic capability of the strains. Use the synchronous RT-PCR method to quantify the toxin production and Nor-1 gene expression level of 17 *Aspergillus flavus* strains, and the results are as shown in Table 5.

Table 5 Results of expression level of toxigenic capability of 17 *Aspergillus flavus* strains and Nor-1 gene by using synchronous RT-PCR method

TABLE 5

Results of expression level of toxigenic capability of 17 *Aspergillus flavus* strains and Nor-1 gene by using synchronous RT-PCR method

| | AFB1 Conc. (ng/mL) ± SD | | Log Nor-1copies ± SD | |
|---|---|---|---|---|
| Strain | Duplex RT-PCR | HPLC | Duplex RT-PCR | Nanodrop |
| 243-2-1 | 241.17 ± 8.13 | 256.79 | 10.63 ± 0.51 | 11.24 |
| 243-2-2 | 204.17 ± 8.13 | 218.48 | 9.59 ± 0.89 | 10.48 |
| IT-1 | 194.71 ± 7.94 | 206.43 | 9.83 ± 0.42 | 10.59 |
| N400 | 189.43 ± 14.37 | 214.80 | 9.15 ± 0.57 | 9.73 |
| N54 | 171.03 ± 6.35 | 186.85 | 8.72 ± 0.34 | 9.50 |
| Pc501 | 151.41 ± 5.18 | 162.45 | 8.70 ± 0.70 | 9.45 |
| N53 | 141.28 ± 12.07 | 154.33 | 9.64 ± 0.80 | 10.11 |
| N271 | 120.97 ± 8.06 | 134.56 | 9.42 ± 0.30 | 9.95 |
| Pg56-1 | 79.69 ± 6.09 | 84.92 | 8.52 ± 0.33 | 9.09 |
| PC124-2 | 66.50 ± 4.93 | 74.29 | 7.85 ± 0.52 | 8.71 |
| Pg14-2 | 45.13 ± 5.04 | 55.56 | 7.31 ± 0.26 | 8.09 |
| 10-2 | 27.23 ± 3.13 | 32.54 | 4.98 ± 0.82 | ND |
| Pc34-1 | 19.69 ± 2.27 | 24.48 | 6.75 ± 0.58 | ND |
| CY1 | $^a$ND | 0 | ND | ND |
| CY2 | ND | 0 | ND | ND |
| Pg28-1 | ND | 0 | 4.84 ± 0.49 | ND |
| Pc321-1-3 | ND | 0 | 6.74 ± 0.87 | ND |
| Control | ND | 0 | ND | ND |

Figure 5:
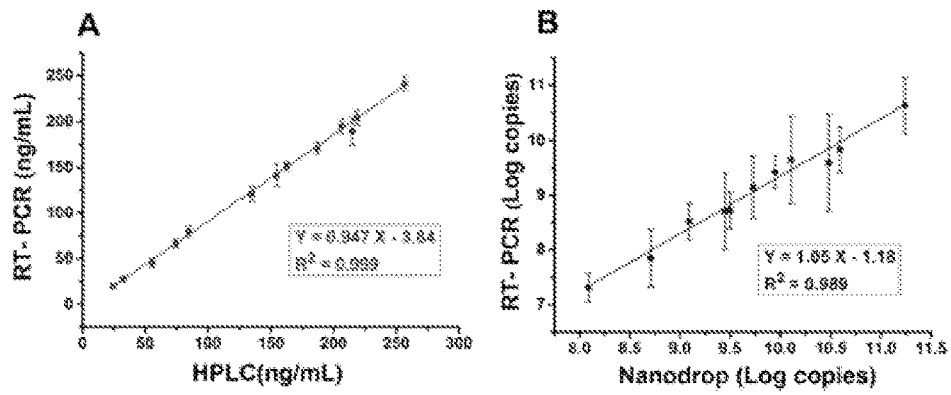
FIG. 5 shows the comparison between quantitative results of synchronous RT-PCR, HPLC and Nanodrop.

In order to verify the accuracy of the results, referring to the method of national standard GB5009.22-2016, a HPLC method is used to quantify the amount of toxin produced by *Aspergillus flavus* strains. Meanwhile, the gene expression of the strain Nor-1 is quantified with a spectrophotometer (Nanodrop). The quantitative results are shown in Table 5. The result is compared with the result obtained through the synchronous RT-PCR method, and the comparison result is shown in A of FIG. 5 and B of FIG. 5. A of FIG. 5 shows the comparison result of RT-PCR and HPLC in quantifying aflatoxin. The linear regression equation obtained is Y=0.947 X-3.84, and the linear regression analysis produces a good correlation ($R2$ =0.999). B of FIG. 5 shows the comparison result of RT-PCR and Nanodrop in quantifying Nor-1 gene transcription. The linear regression equation obtained by the method is Y=1.05 X−1.18, and the correlation coefficient is $R^2$=0.989. The comparison results of different detection methods show that the established synchronous RT-PCR quantitative results are reliable and can be used for the synchronous analysis of toxigenic capability of *Aspergillus flavus* strains and Nor-1 gene transcriptional quantity.

Embodiment 3

1. Use Nor-1 transcriptional quantity and AFT/Nor-1 (the ratio of toxigenic capability to Nor-1 transcriptional quantity) to evaluate the toxigenic capability of *Aspergillus flavus* respectively Through the comparison and analysis of the results, it is found that if the toxigenic capability of *Aspergillus flavus* is evaluated solely from the Nor-1 transcriptional quantity, the identification results are not reliable. For example, the logarithmic values of the copy number of Nor-1 gene expression in *Aspergillus flavus* strains Pc124-2 and Pc34-1 are 7.85±0.52 and 6.75±0.58, respectively. The Nor-1 gene expression levels of the two strains are equivalent. However, the production of aflatoxin of strain Pc124-2 is 66.5±4.93 ng/mL, and the production of aflatoxin of strain Pc34-1 is only 19.69±2.27 ng/ml. In addition, strains CY1, CY2, Pg28-1 and Pc321-1-3 are not found to produce aflatoxin. Nonetheless, the Nor-1 gene levels expressed by strains Pg28-1 and Pc321-1-3 are even higher than those of some strains that produce aflatoxin.

Figure 6:
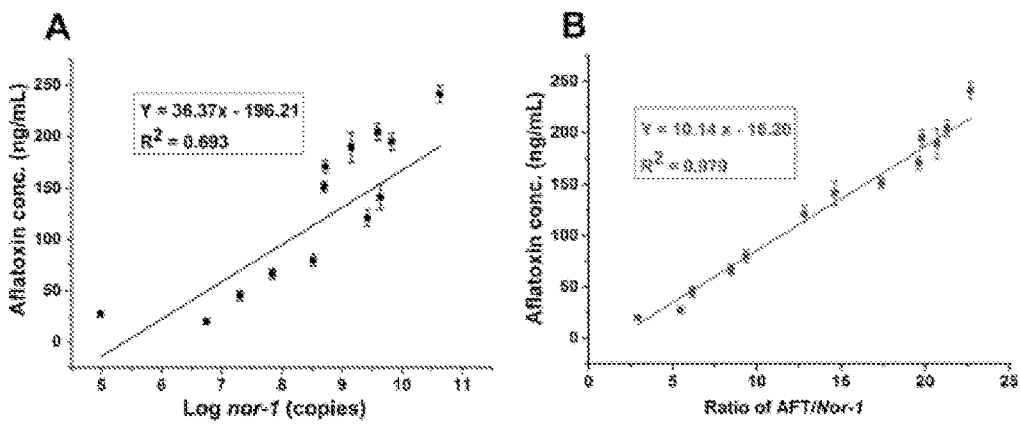
FIG. 6 shows the correlation relationship (A) between aflatoxin yield and Nor-1 gene expression amount, and the correlation relationship (B) between aflatoxin yield and AFT/Nor-1 ratio.

However, it is more reliable to evaluate the toxigenic capability of *Aspergillus flavus* by using the ratio of production of aflatoxin to the expression level of Nor-1 gene. In order to further explore the correlation relationship between the toxigenic capability of *Aspergillus flavus* strains, expression level of Nor-1 gene as well as AFT/Nor-1, the toxigenic capability of strains is taken as the ordinate, and the logarithm of Nor-1 gene expression amount and the ratio of AFT/Nor-1 are used as the abscissa for the diagram. The correlation relationship between toxigenic capability of *Aspergillus flavus* strains and Nor-1 gene expression amount is as shown in A of FIG. 6. The linear regression equation is: y=36.37 x−196.21, and the correlation coefficient generated by linear regression analysis is $R^2=0.693$. However, the correlation relationship between toxigenic capability of *Aspergillus flavus* and the ratio of AFT/Nor-1 is shown in B of FIG. 6. The linear regression equation is: y=10.14 x−16.20, and the correlation coefficient produced by linear regression analysis is $R^2=0.979$. There is an excellent correlation between the toxigenic capability of *Aspergillus flavus* strains and the ratio of AFT/Nor-1.

In light of the above, the disclosure provides that the equation for identifying toxigenic capability of *Aspergillus flavus* strains is: y=10.14 x−16.20, wherein X represents AFT/Nor-1, and Y represents toxigenic capability. For highly toxigenic strains, the toxigenic capability is >150 ng/mL; the medium toxigenic capability: 50<toxigenic capability<150 ng/mL; the low-toxigenic capability: toxigenic capability<50 ng/mL; no production of toxin: 0; then calculate the identification range of toxigenic capability according to the regression equation:

Highly toxigenic strains: AFT/Nor-1>16.4;
Medium toxigenic strains: 6.5<AFT/Nor-1<16.4;
Low toxigenic strains: 0<AFT/Nor-1<6.5;
Non-toxigenic strains: AFT/Nor-1=0.

Verification of stability of AFT/Nor-1 (ratio of toxigenic capability to Nor-1 transcriptional quantity) in identification result of toxigenic capability 2. Verification of stability of AFT/Nor-1 (ratio of toxigenic capability to Nor-1 transcriptional quantity) in identification result of toxigenic capability In order to further verify the stability of AFT/Nor-1 ratio in identifying the results of toxigenic capability, intra-group and inter-group experimental analyses are respectively performed to five *Aspergillus flavus* strains in terms of toxigenic capability of aflatoxin and Nor-1 gene transcriptional quantity. In the intra-group experiment, 5 replicates are set in parallel on the same day, and the average value of the 5 replicates is used as the toxigenic capability and [nor-1] Nor-1 gene transcriptional quantity of the batch of strains. Three different dates are set for the inter-group experiment, each date is set as a batch, and a total of 3 batches are set. The results are shown in Table 6.

TABLE 6

Verification of stability of AFT/Nor-1 (ratio of toxigenic capability to Nor-1 transcriptional quantity) in identification result of toxigenic capability

| strain | Aflatoxin (ng/mL) | | | *CV (%) | Log Nor-1 (copies) | | | #CV (%) | Ratio (AFT/Nor-1) | | | &CV (%) |
|---|---|---|---|---|---|---|---|---|---|---|---|---|
| | [1]AFT | [2]AFT | [3]AFT | | [1]Nor-1 | [2]Nor-1 | [3]Nor-1 | | [1]Ratio | [2]Ratio | [3]Ratio | |
| IT-1 | 169.55 | 210.29 | 194.71 | 10.73 | 8.01 | 9.76 | 9.83 | 11.21 | 21.17 | 21.55 | 19.81 | 4.39 |
| N54 | 180.82 | 158.33 | 171.03 | 6.63 | 9.69 | 8.20 | 8.72 | 8.52 | 18.67 | 19.31 | 19.60 | 2.51 |
| IT-2 | 104.92 | 84.68 | 75.27 | @17.16 | 8.65 | 7.99 | 6.74 | 12.48 | 12.13 | 10.60 | 11.17 | 6.84 |
| Pg56-1 | 54.45 | 53.17 | 79.96 | @24.17 | 6.93 | 5.59 | 8.52 | @20.91 | 7.86 | 9.51 | 9.38 | 10.32 |
| N220 | 28.67 | 41.09 | 21.15 | @33.23 | 6.17 | 7.68 | 5.07 | @20.78 | 4.65 | 5.35 | 4.17 | 12.56 |
| 233-1 | 10.07 | 19.69 | 25.32 | @42.00 | 4.09 | 8.26 | 8.46 | @35.57 | 2.46 | 2.38 | 2.99 | 12.68 |

Note:
[1]AFT production of aflatoxin in the first batch;
[2]Nor-1 Nor-1 gene transcriptional quantity of the second batch;
[3]Ratio AFT/Nor-1 ratio of the third batch;
*CV, #Cy, &CV respectively represent the production of aflatoxin, Nor-1 gene transcriptional quantity and coefficient of variation of AFT/Nor-1 ratio detected from different batches;
@The coefficient of variation (CV) is greater than 15%.

The amount of aflatoxigenic capability and Nor-1 gene transcriptional quantity in the table are the average of 5 repeated intra-group experiments.

From the table, it can be easily found that there is a big difference between the aflatoxin yield produced by different culture batches and Nor-1 gene transcriptional quantity. Taking strain 233-1 as an example, the yields of aflatoxin detected in the three batches are 10.07, 19.69, and 25.32 ng/mL, respectively, and the coefficient of variation between the different batches is 42.00%. In addition, for the yields of aflatoxin produced by the strains IT-2, Pg56-1-2, N200 and 233-1, the intra-group coefficients of variation between different batches are all larger than 17.00%. It can be seen that it is unreliable to evaluate the toxigenic capability of strains from the aflatoxin yield produced alone. By analogy, based on the inter-group Nor-1 gene transcriptional quantity between different batches, it can be found that there is a big difference between Nor-1 gene transcriptional quantity, which equivalently proves that it is not reliable to identify and evaluate the toxigenic capability of strains solely from the Nor-1 gene transcriptional quantity. However, the inter-group coefficients of variation of AFT/Nor-1 ratio are less than 13%, which has better stability.

In summary, the method for identifying and evaluating the toxigenic capability of toxigenic strains of aflatoxin provided in the disclosure, that is, the AFT/Nor-1 ratio identification, is a more accurate and reliable method for identifying and evaluating the toxigenic capability of *Aspergillus flavus* strains.

Obviously, the above-mentioned embodiments are merely examples for clear description, and are not intended to limit the implementation. For those of ordinary skill in the art, other changes or changes in different forms can be made on the basis of the above description. It is unnecessary and impossible to list all implementation methods here. Therefore, obvious changes or alterations of the disclosure still fall within the protection scope of the disclosure.

What is claimed is:

1. A method for identifying and evaluating toxigenic capability of aflatoxigenic strain, comprising:

culturing *Aspergillus flavus* strains to obtain an *Aspergillus flavus* spores solution; culturing the *Aspergillus flavus* spores solution; and then filtering to obtain a strain culture solution containing aflatoxin and a fungus ball after the shaking culture is completed;

measuring an aflatoxin yield of the strain culture solution and a Nor-1 gene transcriptional quantity of the fungus ball to obtain a ratio of the aflatoxin yield to the Nor-1 gene transcriptional quantity; and identifying and evaluating the toxigenic capability of the aflatoxigenic strain according to the ratio of the aflatoxin yield to the Nor-1 gene transcriptional quantity, wherein when the ratio is greater than 16.4, it indicates that the aflatoxigenic strain is a highly toxigenic strain having a toxigenic capability greater than 150 ng/mL; when the ratio is greater than 6.5 and less than 16.4, it indicates that the aflatoxigenic strain is a medium toxigenic strain having a toxigenic capability greater than 50 ng/ml and less than 150 ng/ml; when the ratio is greater than 0 and less than 6.5, it indicates that the aflatoxigenic strain is a low toxigenic strain having a toxigenic capability less than 50 ng/mL; when the ratio is 0, it indicates that the aflatoxigenic strain is a non-toxigenic strain, wherein the aflatoxin yield and the Nor-1 gene transcriptional quantity is measured through a synchronous detection RT-PCR method, and the synchronous detection RT-PCR method comprises the following steps:

(1) establishing an S-type standard curve for quantifying aflatoxin by the following steps: performing an immune competition reaction using aflatoxin standard products of different concentrations, a phage having surface-displaying aflatoxin anti-idiotypic nano antibody and an aflatoxin monoclonal antibody of constant amount, wherein the aflatoxin standard products compete with the phage to bind to the aflatoxin monoclonal antibody; eluting the phage bound to the aflatoxin monoclonal antibody to obtain eluates after the immune competition reaction is over, wherein the aflatoxin standard products of different concentrations correspond to different amounts of eluted phage in the eluates; performing a synchronous RT-PCR amplification reaction to obtain different first Ct values using DNA molecules of the eluted phage as amplification targets in each of the eluates separately; and performing a regression analysis to obtain the S-type standard curve using a logarithm of the different concentrations of the aflatoxin standard products as abscissa and the different first Ct value as ordinate;

(2) establishing a RT-PCR standard curve for Nor-1 gene transcriptional quantity by the following steps: serially diluting samples of known copy number of Nor-1 gene DNA fragment (Tq-nor1) into different copy numbers; performing the synchronous RT-PCR amplification reaction to obtain different second Ct values using each copy number of the Tq-nor1 separately; and performing a regression analysis to obtain the RT-PCR standard curve using a logarithm of the different copy number of the Tq-nor1 as abscissa and the different second Ct value as ordinate;

(3) diluting the strain culture solution containing the aflatoxin; performing another immune competition reaction using the diluted strain culture solution, a phage having surface-displaying aflatoxin anti-idiotypic nano antibody and aflatoxin monoclonal antibody of constant amount, wherein the aflatoxin competes with the phage to bind to the aflatoxin monoclonal antibody; eluting the phage bound to the aflatoxin monoclonal antibody to obtain eluate after the immune competition reaction is over; performing a synchronous RT-PCR amplification reaction to obtain a third Ct value using DNA molecule of the eluted phage as amplification template; additionally, drying the fungus ball, extracting a total RNA from the dried fungus ball, and reverse transcribing the total RNA into cDNA; and performing synchronous RT-PCR amplification reaction to obtain a fourth Ct value using the cDNA as amplification template; calculating the aflatoxin yield corresponding to the third Ct value using the S-type standard curve; and calculating Nor-1 gene transcriptional quantity corresponding to the fourth Ct value using the RT-PCR standard curve;

wherein in the reaction system of the synchronous RT-PCR amplification reaction, primers used to amplify Nor-1 gene DNA fragment (Tq-nor1) are as follows:

upstream primer Tq-nor1-F, wherein the nucleotide sequence of the upstream primer Tq-nor1-F is SEQ ID NO: 4; and downstream primer Tq-nor1-R, wherein the nucleotide sequence of the downstream primer Tq-nor1-R is SEQ ID NO: 5;

wherein in the reaction system of the synchronous RT-PCR amplification reaction, primers used to amplify the DNA molecules released by the phage surface-displaying aflatoxin anti-idiotypic nano antibody are as follows:

upstream primer Ph-F, wherein the nucleotide sequence of the upstream primer Ph-F is SEQ ID NO: 1; and downstream primer Ph-R, wherein the nucleotide sequence of the downstream primer Ph-R is SEQ ID NO: 2.

2. The method for identifying and evaluating toxigenic capability of the aflatoxigenic strain according to claim 1, wherein the phage surface-displaying aflatoxin anti-idiotypic nano antibody is phage VHH 2-5, and the aflatoxin monoclonal antibody is aflatoxin monoclonal antibody 1C11.

3. The method for identifying and evaluating toxigenic capability of the aflatoxigenic strain according to claim 1, wherein in the reaction system of the synchronous RT-PCR amplification reaction, a final concentration of upstream and downstream primers: Ph-F, Ph-R, Tq-nor1-F, and Tq-nor1-R is 300 to 400 nM; fluorescent probe: a final concentration of Ph-probe and Tq-probe is 200 to 400 nM; final dosage of DNA polymerase: 0.5 U to 1.0 U; a final concentration of $MgCl_{2: 1}$ mM to 2 mM; a final concentration of dNTPs: 200 uM to 400 uM, wherein the nucleotide sequence of fluorescent probe Ph-probe is SEQ ID NO: 3; the nucleotide sequence of fluorescent probe Tq-probe is SEQ ID NO: 6.

4. The method for identifying and evaluating toxigenic capability of the aflatoxigenic strain according to claim 1, wherein the reaction system of the synchronous RT-PCR amplification reaction comprises: universal probe qPCR master mix 5 μL, Ph-F 0.1 μL, Ph-R 0.1 μL, Ph-probe 0.1 μL, phage template 2 μL, Tq-nor1-F 0.1 μL, Tq-nor1-R 0.1 μL, Tq-probe 0.1 μL, Nor-1 gene template 1 μL, DNA polymerase 0.2 μL, $MgCl_2$ 0.8 μL, dNTPs 0.2 μL, and $H_2O$ to a final volume of 10 μL, wherein the nucleotide sequence of fluorescent probe Ph-probe is SEQ ID NO: 3; the nucleotide sequence of fluorescent probe Tq-probe is SEQ ID NO: 6.

* * * * *

```
                           SEQUENCE LISTING

<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: A nucleotide sequence of the upstream primer
      Ph-F

<400> SEQUENCE: 1
gtggtagcac aaactatg                                                  18

<210> SEQ ID NO 2
<211> LENGTH: 18
<212> TYPE: DNA
<213> ORGANISM: Artificial Sequence
<220> FEATURE:
<223> OTHER INFORMATION: A nucleotide sequence of the downstream primer
      Ph-R

<400> SEQUENCE: 2
ggctgcacag taataaac                                                  18

<210> SEQ ID NO 3
<211> LENGTH: 23
<212> TYPE: DNA
<213> ORGANISM: Artificial Sequence
<220> FEATURE:
<223> OTHER INFORMATION: A nucleotide sequence of fluorescent probe Ph-
      probe

<400> SEQUENCE: 3
ccgattcacc atctccagag aca                                            23

<210> SEQ ID NO 4
<211> LENGTH: 20
<212> TYPE: DNA
<213> ORGANISM: Artificial Sequence
<220> FEATURE:
<223> OTHER INFORMATION: A nucleotide sequence of the upstream primer
      Tq-nor1-F

<400> SEQUENCE: 4
gtccaagcaa caggccaagt                                                20

<210> SEQ ID NO 5
<211> LENGTH: 20
<212> TYPE: DNA
<213> ORGANISM: Artificial Sequence
<220> FEATURE:
<223> OTHER INFORMATION: A nucleotide sequence of the downstream primer
      Tq-nor1-R

<400> SEQUENCE: 5
tcgtgcatgt tggtgatggt                                                20

<210> SEQ ID NO 6
<211> LENGTH: 18
<212> TYPE: DNA
<213> ORGANISM: Artificial Sequence
```

```
<220> FEATURE:
<223> OTHER INFORMATION: A nucleotide sequence of fluorescent probe
      Tq-probe

<400> SEQUENCE: 6
tgtcttgatc ggcgcccg                                                 18

<210> SEQ ID NO 7
<211> LENGTH: 25
<212> TYPE: DNA
<213> ORGANISM: Artificial Sequence
<220> FEATURE:
<223> OTHER INFORMATION: A nucleotide sequence of the upstream primer
      Nor1-F

<400> SEQUENCE: 7
accgctacgc cggcactctc ggcac                                         25

<210> SEQ ID NO 8
<211> LENGTH: 25
<212> TYPE: DNA
<213> ORGANISM: Artificial Sequence
<220> FEATURE:
<223> OTHER INFORMATION: A nucleotide sequence of the downstream primer
      Nor1-R

<400> SEQUENCE: 8
gttggccgcc agcttcgaca ctccg                                         25
```